US00PP15218P2

(12) United States Plant Patent
Nixon

(10) Patent No.: US PP15,218 P2
(45) Date of Patent: Oct. 12, 2004

(54) ***ZOYSIAGRASS* PLANT NAMED 'SOUTHERN GEM'**

(50) Latin Name: *Zoysia japonica*
Varietal Denomination: Southern Gem

(76) Inventor: Ronald Nixon, 2405 Hwy. 82, Midway, AL (US) 36053

( * ) Notice: Subject to any disclaimer, the term of this patent is extended or adjusted under 35 U.S.C. 154(b) by 68 days.

(21) Appl. No.: 10/704,033

(22) Filed: Nov. 10, 2003

(51) Int. Cl.[7] ..... A01H 5/00
(52) U.S. Cl. ..... Plt./390
(58) Field of Search ..... Plt./390

*Primary Examiner*—Anne Marie Grunberg
*Assistant Examiner*—Annette H Para

(57) ABSTRACT

An asexually reproduced variety of perennial *zoysiagrass* with a unique combination of characters including fine to medium leaf blade width, and low floral production.

2 Drawing Sheets

Latin name of the genus and species of the plant claimed: The present invention relates to the genus and species *Zoysia japonica* (L.) Merr.

Variety denomination: 'Southern Gem'.

BACKGROUND OF THE INVENTION

Field of the Invention

The present invention relates to a new and distinct asexually reproduced variety of perennial *zoysiagrass* (*Zoysia japonica* (L.)) Merr.

BRIEF SUMMARY OF THE INVENTION

Background of the Invention

This invention relates to a new and distinct perennial *zoysiagrass* cultivar identified as 'Southern Gem' *zoysiagrass* (herein referred to as 'Southern Gem'). The inventor, Ronald Nixon, discovered 'Southern Gem' under cultivated conditions in a sod field near Midway, Ala. 'Southern Gem' was identified as a distinctly different vegetative patch or segregated clonal plant differing by finer leaf texture from the suspected parental variety 'Meyer' (unpatented). The inventor asexually reproduced 'Southern Gem' by taking vegetative cuttings of the plant material from the field including stolons and rhizomes, cutting the rhizomes and stolons into segments, each with a vegetative bud, and rooted them in potting media near Midway. Ala. Another *zoysiagrass* discovered by Ronald Nixon, the variety 'Marion', is the subject of the co-pending U.S. Plant patent application, having application Ser. No. 10/091,876. Another *zoysiagrass* discovered by Ronald Nixon, the variety 'Serene', is the subject of the co-pending U.S. Plant patent application, having application Ser. No. 10/093,810.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is *Zoysiagrass* plant named 'Southern Gem'.

BRIEF DESCRIPTIONS OF THE ILLUSTRATIONS

Figure 1:
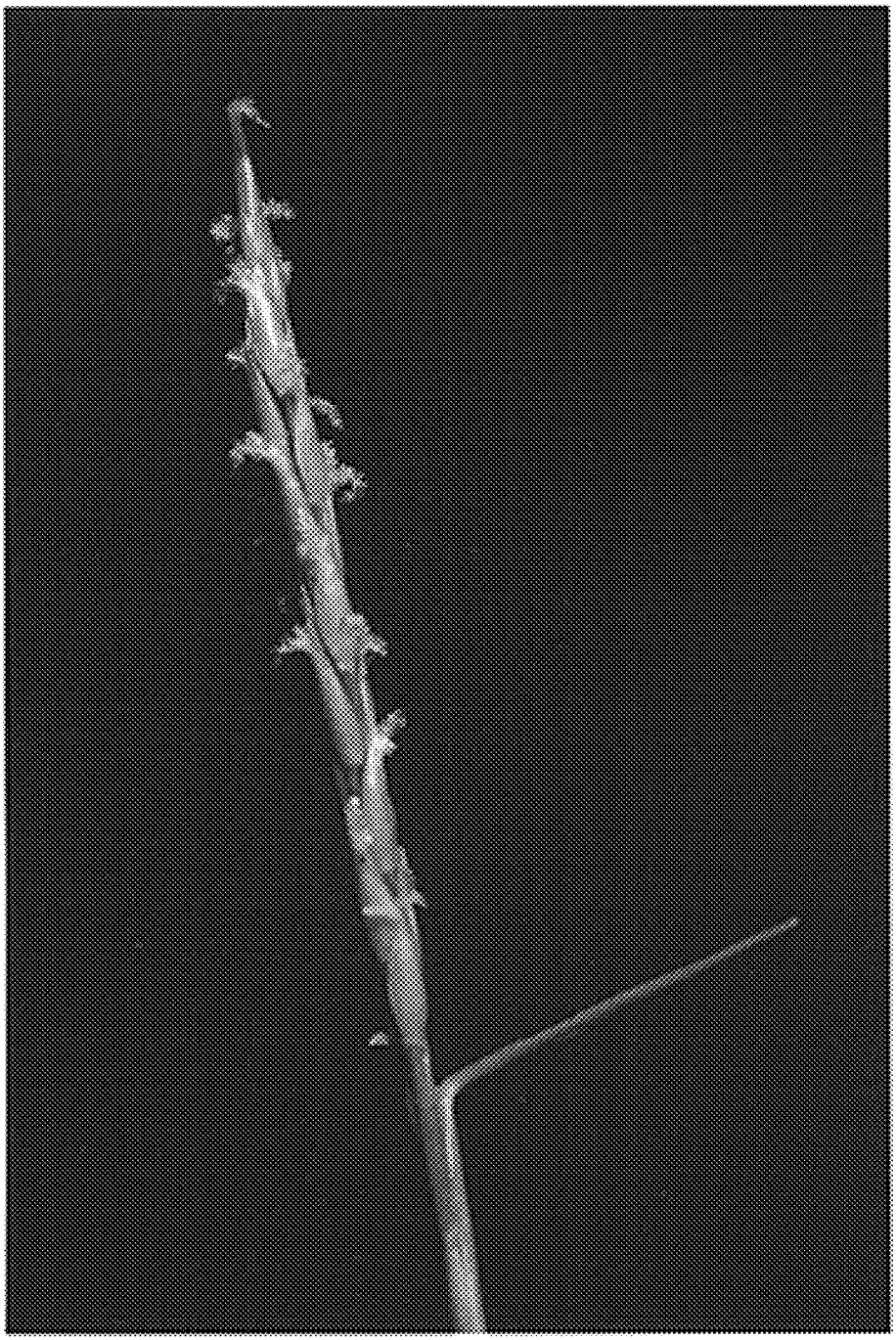

FIG. 1. Inflorescence of 'Southern Gem' *zoysiagrass*.

Figure 2:
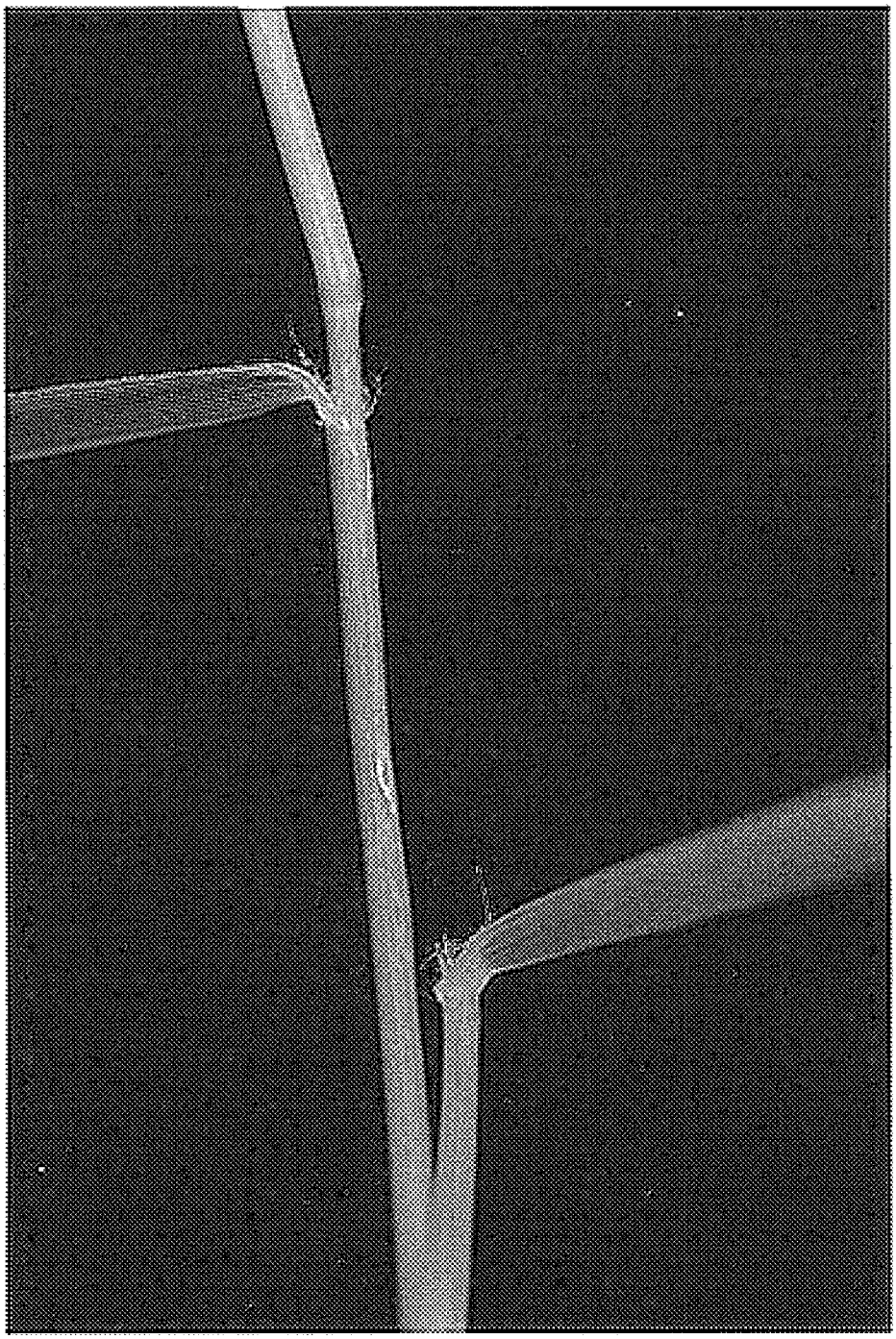

FIG. 2. Tiller of 'Southern Gem' *zoysiagrass* with leaf characters.

COMPLETE DESCRIPTION OF THE VARIETY

'Southern Gem' was characterized in greenhouse and field conditions. 'Southern Gem' is a unique variety of *zoysiagrass* (*Zoysia japonica* (L.)) Merr. that was discovered under cultivated conditions in a sod field. 'Southern Gem' was identified in the field as having a finer leaf texture than its suspected parent 'Meyer'. The sod field was located in USDA Plant Hardiness Zone 8A. 'Southern Gem' was propagated by the inventor under field and greenhouse conditions in Midway, Ala. by cutting of rhizomes and stolons, rooting them in soil, and planting of the rooted material to provide planting stock for studying performance and for comparison of morphological characters after propagation. 'Southern Gem' has been propagated by rhizomes, stolons, tillers, and sod. Asexually reproduced plants of 'Southern Gem' have remained stable and true to type through successive generations of propagation. No seedling establishment from 'Southern Gem' has been noticed in either greenhouse or field studies.

'Southern Gem' is a perennial *zoysiagrass* that spreads by both stolons and rhizomes. Characteristics of 'Southern Gem' measured in 2003 were taken from plants that were approximately 9 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20–20–20 in two equal soluble applications per month.

'Southern Gem' has a finer leaf texture than the suspected parent 'Meyer' and 'El Toro' (Table 1) with a wider leaf blade than 'Cashmere' (unpatented), 'Diamond', 'Emerald' (unpatented), or 'Cavalier' when measured under greenhouse conditions in Lebanon, Oreg. 'Southern Gem' has a shorter floral area than 'Meyer' and 'El Toro', with shorter anthers than 'Meyer' (Table 2) and longer anthers than 'Diamond'. 'Southern Gem' has adaxial surface leaf hairs compared to the varieties 'Cashmere' and 'Royal' that have no leaf hairs. The leaf hairs of 'Southern Gem' are shorter than 'Meyer' and 'Emerald' and 'Marion' (Table 3). No seeds of 'Southern Gem' have developed; no seedlings have been noted in the field production area. The inflorescences produced in the greenhouse have consisted of empty florets and no seed has been formed.

'Southern Gem' has not shown any susceptibility in tests to date in the Midway, Ala. production site to the diseases and insects common to the *zoysiagrass* genus. 'Southern Gem' shows turf density similar to 'Cashmere'. 'Southern Gem' has shown good turfgrass performance and temperature adaptation when tested as far north as Midway, Ala. USDA zone 8A, which would extend the area of adaptation for 'Southern Gem' in a line from South-Central Alabama across central Arkansas through Central Texas in an East/West line and on a North/South line from South central Alabama south through Mexico. 'Southern Gem' will be limited only by winter survival in colder regions. 'Southern Gem' is similar to most medium to fine textured *zoysiagrasses* in water use demands as shown in production situations, and will be limited by adequate precipitation in drier to arid regions. 'Southern Gem' is adapted from sandy to heavier loam soil textures and from slightly acid to slightly alkaline soil pH.

TABLE 1

Leaf blade widths and lengths and texture class of selected *zoysiagrass* cultivars, measured under greenhouse conditions in Lebanon, OR, 2003.

| Variety | Width. 2nd youngest stolon leaf mm | Length, 2nd youngest stolon leaf cm | Length, 3rd youngest crown leaf cm | Width, 3rd youngest crown leaf mm | Leaf Texture Class |
|---|---|---|---|---|---|
| 'Southern Gem' | 2.36 | 3.03 | 4.40 | 2.27 | Fine–Medium |
| 'Cashmene' | 1.65 | 3.81 | 3.68 | 1.89 | Fine |
| 'Diamond' | 1.76 | 3.27 | 2.02 | 1.13 | Very Fine |
| 'Emerald' | 1.80 | 2.54 | 4.85 | 2.10 | Fine |
| 'Royal' | 1.88 | 2.60 | 1.92 | 1.63 | Very Fine |
| 'Cavalier' | 2.08 | 3.59 | 2.15 | 1.87 | Very Fine |
| 'Marion' | 2.65 | 3.68 | 4.97 | 2.83 | Fine–Medium |
| 'Meyer' | 2.95 | 3.29 | 6.47 | 3.64 | Medium–Coarse |
| 'Serene' | 2.61 | 3.68 | 4.17 | 2.47 | Fine–Medium |
| 'El Toro' | 3.77 | 5.45 | 3.80 | 3.32 | Medium–Coarse |
| t, p = 0.05 | 0.060 | 1.170 | 2.370 | 0.150 | |

TABLE 2

Inflorescence and leaf characters of selected *zoysiagrass* cultivars, measured under greenhouse conditions in Lebanon, OR, 2003.

| Variety | Length floral area cm | Length, flag leaf collar to first lower node mm | Sheath length, crown leaf cm | Anther length mm | Node width at base of inflorescence mm |
|---|---|---|---|---|---|
| 'Southern Gem' | 2.07 | 3.11 | 1.73 | 1.43 | 0.61 |
| 'Emerald' | 1.44 | 4.15 | 1.81 | 1.29 | 0.76 |
| 'Cashmere' | 1.76 | 13.48 | 1.40 | 1.31 | 0.60 |
| 'Marion' | 1.98 | 7.27 | 2.14 | 1.49 | 0.72 |
| 'Serene' | 2.05 | 9.30 | 1.51 | 1.42 | 0.74 |
| 'Meyer' | 3.10 | 3.78 | 1.80 | 2.17 | 0.78 |
| 'Crowne' | 3.16 | 9.00 | 1.74 | 3.50 | 0.72 |
| 'El Toro' | 3.78 | 8.38 | 1.53 | 1.50 | 0.99 |
| t, p = 0.05 | 0.128 | 2.710 | 0.131 | 0.010 | 0.013 |

TABLE 3

Internode lengths and adaxial leaf hair length measurements of selected *zoysiagrass* cultivars, measured under greenhouse conditions in Lebanon, OR, 2003

| Variety | Hair length, adaxial leaf mm | Stolon Internode length, node2–3 cm | Stolon Internode length, node3–4 cm |
|---|---|---|---|
| 'Southern Gem' | 1.11 | 1.56 | 2.15 |
| 'Serene' | 0.917 | 1.640 | 1.22 |
| 'Marion' | 1.339 | 0.950 | 1.10 |
| 'Emerald' | 2.153 | 1.000 | 1.02 |
| 'Cashmere' | 0.000 | 1.987 | 1.50 |
| 'Meyer' | 1.767 | 1.900 | 2.02 |
| 'Royal' | 0.000 | 1.580 | 1.90 |
| 'Crowne' | 1.247 | 1.800 | 1.52 |
| 'Cavalier' | 2.029 | 1.729 | 1.63 |
| 'El Toro' | 1.263 | 1.350 | 1.00 |
| t, p = 0.05 | 0.080 | 0.126 | 0.12 |

COMPLETE BOTANICAL DESCRIPTION OF THE VARIETY

Origin: 'Southern Gem' is a cultivar of a single clone discovered under cultivated conditions in Midway, Ala. in a sod field of 'Meyer' *zoysiagrass*.

Classification: *Zoysia japonica* (L.) Merr.

Growth habit: 'Southern Gem' is a perennial plant that spreads by stolons and rhizomes and produces a dense, medium to fine textured turfgrass. The inflorescence of 'Southern Gem' is a terminal spike-like raceme, with spikelets on short pedicels.

Leaf Blade: rolled in the bud, slightly concave surface.

Leaf blade pubescence: Adaxial leaf surface has very few (1–4; some with 0) hairs approximately 1.1 mm in length; hairs absent on abaxial leaf surface.

Leaf sheath pubescence: few long hairs at mouth of sheath approximately 3.1 mm length.

Leaf blade margin: very slight roughness with small serrations.

Leaf blade veins: obscure.

Leaf ligule hairs: up to 1.5 mm in length, 5 to 7 in number in center of ligule.

Leaf blade flexibility (softness): stiff.

Vegetative leaf, third youngest vegetative leaf:

*Blade length mean.*—4.40 cm.

*Blade width mean.*—2.27 mm.

*Sheath length mean.*—1.73 cm.

Stolon leaf angle, third youngest leaf: 74.5 degrees (Meyer: 98.1; El Toro: 100.6).

Stolon internode length, node 2–3: 1.56 cm.

Stolon internode length, node 3–4: 2.15 cm.

Stolon internode width, node 2–3: 1.19×1.35 mm.

Stolon internode width, node 3–4: 1.23×1.32 mm.

Inflorescence characters:

*Culm total length, including floral area to node below flag leaf.*—2.93 cm. Length of stem of inflorescence: 0.86 cm Floral area length: 2.07 cm.

*Culm width, stem thickness, base of floral area.*—0.61 mm.

*Anther length.*—1.43 mm.

*Floret (seed) length.*—2.78 mm.

*Node thickness, node below flag leaf.*—0.90 mm.

Mature plant height, including inflorescence: 11.3 cm; Marion: 18.8 cm; Meyer: 15.0 cm Color notations, vegetative characters, based on The R.H.S. Colour Chart (light quality, photoperiod, and general growth of the plants affect color notations):

*Leaf blade color adaxial leaf surface.*—137A green.

*Leaf blade color abaxial leaf surface.*—137A green.

*Stolon color.*—59A red purple and 146D yellow green.

Color notations, floral characters, based on The R.H.S. Colour Chart (light quality, photoperiod, and general growth of the plants affect color notations):

*Culm stalk.*—146D yellow green.

*Matured spikelet* (*lemma on seed*).—161D greyed yellow.

*Stigma.*—155D white.

*Anthers, mature, dried.*—155C white.

Turf quality (rated 1–9, 9 best): 7.6; 'Meyer': 5; 'El Toro': 4.5.

Turf color (rated 1–9, 9 best): 6; 'Meyer': 5; 'El Toro': 4.

Turf density establishment rating (rated 1–9, 9 best): 5.0; 'Meyer': 4; 'El Toro': 4.

Leaf texture rating (rated 1–9, 9 best): 7; 'Meyer': 4; 'Diamond': 9.

References Cited
U.S. Patent Documents

| | |
|---|---|
| October, 1998. Engelke, M. C. | U.S. PP 10,636. 'Diamond' *zoysiagrass* |
| October, 2000. Engelke, M. C. | U.S. PP 11,570. 'Crowne' *zoysiagrass* |
| December, 1986. Youngner, V. B. | U.S. PP 5,845. 'El Toro' *zoysiagrass* |
| September, 2000. Engelke, M. C. | U.S. PP 11,515. 'Palisades' *zoysiagrass* |

I claim:

1. A new and distinct variety of *zoysiagrass* plant, substantially as described and illustrated herein, characterized particularly with the unique combination of morphological characters.

* * * * *